United States Patent
Markman

[19]

[11] Patent Number: 6,056,736

[45] Date of Patent: May 2, 2000

[54] DEVICE AND METHOD FOR LOADING HAIR GRAFTS INTO A CARTRIDGE

[76] Inventor: Barry S. Markman, 5157 Jarom, Las Vegas, Nev. 89120

[21] Appl. No.: 09/183,000

[22] Filed: Oct. 29, 1998

[51] Int. Cl.[7] .................................................. A61B 17/00
[52] U.S. Cl. ............................................... 606/1; 606/187
[58] Field of Search ................... 606/1, 131, 184, 606/185, 186, 187; 623/15

[56] References Cited

U.S. PATENT DOCUMENTS

| | | | |
|---|---|---|---|
| 5,464,411 | 11/1995 | Schulte et al. | 606/130 |
| 5,782,851 | 7/1998 | Rassman | 636/167 |
| 5,792,169 | 8/1998 | Markman | 606/186 |

*Primary Examiner*—Michael Buiz
*Assistant Examiner*—Jennifer Maynard
*Attorney, Agent, or Firm*—Milbank, Tweed, Hadley & McCloy LLP

[57] ABSTRACT

A device and method are provided for loading harvested hair grafts into a cartridge which includes a fixture to hold the cartridge receiving the grafts. A vacuum source imposes a differential pressure across the cartridge to urge grafts into the openings of the cartridge. A blocking template has at least one provided to register the openings to prevent the grafts received from exiting the openings due to the differential pressure.

7 Claims, 1 Drawing Sheet

DEVICE AND METHOD FOR LOADING HAIR GRAFTS INTO A CARTRIDGE

FIELD OF THE INVENTION

The present invention relates to devices and method for loading hair grafts into cartridges for subsequent transplantation thereof

BACKGROUND

As described in U.S. Pat. No. 5,792,169 issued Aug. 11, 1998 to the applicant herein, the disclosure of which is hereby incorporated by reference, a hair graft transplantation device has been developed wherein a supply of harvested hair grafts are retained in a cartridge. During the transplantation, the grafts are moved from the cartridge into a dilated graft site. In that a supply of grafts is provided by the cartridge, the grafting procedure time is shortened and a greater number of grafts can transplanted in a session.

Th cartridge includes a number of openings each adapted to hold a hair graft. Heretofore, I loaded the grafts into their individual openings by using forceps to insert the graft and push them into the opening to nest therein. This procedure is time consuming. There is a need for a device and method to increase the rate at which the grafts can be loaded into the cartridge. Increasing the speed will not only save time but reduce the time the grafts are exposed to the environment decreasing the risk of infection and loss of viability of the graft.

SUMMARY OF THE INVENTION

There is, therefor, set forth according to the present invention a device and method for loading hair grafts into a cartridge for transplantation thereof which facilitates and expedites loading of grafts.

Accordingly the device includes a fixture adapted to hold a cartridge. Means are provided for imposing a vacuum at one side of the cartridge to draw a graft into a selected opening in the cartridge. To prevent the graft from being drawn through the openings a blocking template is disposed between the cartridge and the vacuum means, the template including a bore of a size to permit the vacuum to be imposed at the opening while at the same time preventing the graft from being drawn from its selected opening. Means may also be provided to block the imposition of the vacuum from the vacuum means on selected openings such as those which have previously been loaded with grafts.

The method includes imposing a vacuum at one side of the cartridge to draw a graft into the opening and confining the graft into the opening with a blocking template. The method also may include closing certain of the openings to the vacuum such as those which have already been loaded with a graft.

The device and method of the present invention enables grafts to be quickly and easily loaded into cartridge openings by imposing the vacuum and positioning the graft at the opening. The vacuum draws the graft into the opening for subsequent transplantation. Furthermore unused openings or openings which have previously been loaded can be blocked from the vacuum to increase the efficiency of the vacuum and to prevent air from being drawn past loaded grafts which may increase the risk of infection or effect the viability of the loaded graft.

BRIEF DESCRIPTION OF THE DRAWINGS

These and other features and advantages of the present invention will become better appreciated as the same becomes better understood with reference to the specification, drawings and claims wherein:

DESCRIPTION

Figure 1:
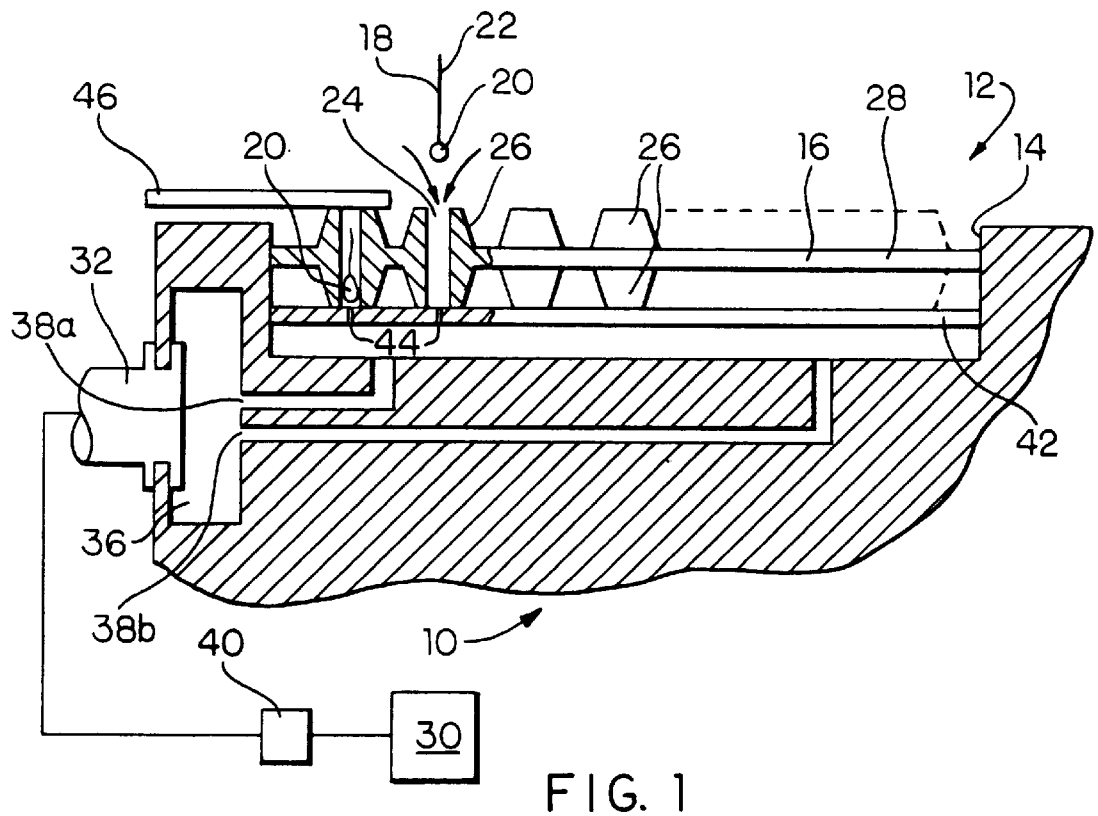
FIG. 1 is a partial side section view of the device according to the present invention.

Turning to the drawings, FIG. 1 shows a partial side section view of a device 10 according to the present invention. The device 10 includes a fixture 12, which may be a well 14 sized to closely receive and seal the side margins of a rectangular cartridge 16 or may include pins, clamps or other suitable structure to retain the cartridge 16 for loading of hair grafts 18. Each of said grafts 18 includes a root bulb 20 having one or more hairs 22. The grafts 18 are preferably previously cultivated from, for example, the nape of the neck.

Figure 2:
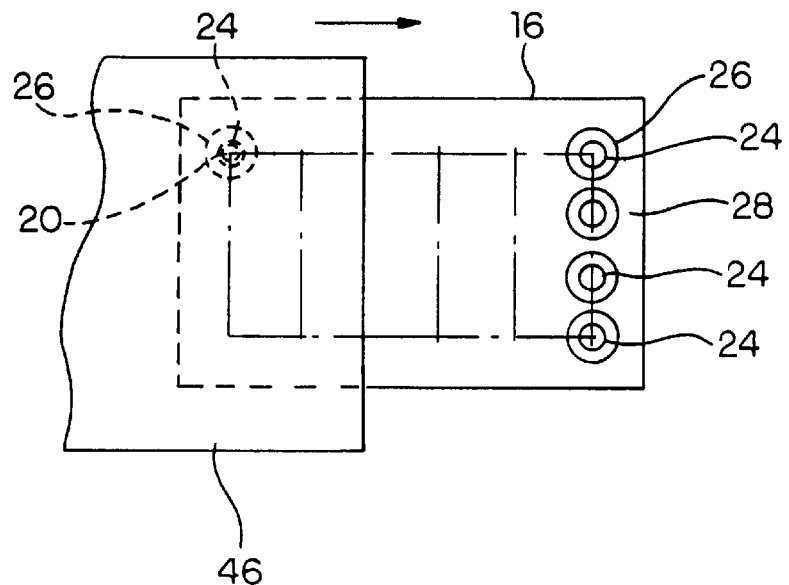
FIG. 2 is a top plan view of the device of FIG. 1.

The cartridge 16 may be circular, square, rectangular or may be in the form of a strip including a plurality of openings 24 each sized and disposed to retain a graft 18. The openings are located and spaced to register with a transplantation device such as of the type described in my U.S. Pat. No. 5,792,169 previously incorporated by reference herein. As suggested in FIG. 2. The openings 24 may be located in the form of a matrix. For transplantation, each graft 18 is urged from its opening 24, downwardly in FIG. 1, by a rod or needle into a dilated graft site. The rod is withdrawn leaving the graft 18 in the graft site.

To provide for registry with the rods for the transplantation device (not shown) and to provide for an elongated opening 24, the cartridge 16 includes a conical boss 26 disposed in axial alignment with each opening 24 as shown in FIG. 1. The bosses 26 project from either side of the planar body 28 for the cartridge 16. It is to be understood that the cartridge 16 could have other suitable shapes to accommodate the graft 18.

The bottom of the well 14 is in communication with a vacuum source such as a vacuum pump 30. Pump 30 communicates with a coupling 32 to the device 10 and, in turn, to a manifold 34 adapted to impose a vacuum at one side of the cartridge 16 in the fixture 12. The manifold 34 includes a header 36 and conduits 38a, b to distribute the vacuum to the underside of the cartridge 16 as retained by the fixture 12.

To control the imposition of the vacuum by the pump 30, a control valve 40 operated by a hand or foot control may be provided.

Disposed in the well 14 proximate the underside of the cartridge 16 is a blocking template 42. The blocking template 42 is adapted to mate with the underside of the cartridge 16 in the well 14. The bosses 26 at the underside of the cartridge 16 rest on the template 42 as shown in FIG. 1. The template 42 has a plurality of bores 44 positioned to register with the openings 24 when the cartridge 16 is disposed in the well 14. Each bore 44 is smaller than the graft 18 and is adapted to prevent the graft 18 from being drawn through the opening 24 into the well and provide a stop therefor.

To load the cartridge 16, the cartridge 16 is placed in the fixture 12 for the device 10 to nest in the well 14. The sides of the cartridge 16 are preferably sealed in any suitable manner such as by providing a resilient seal about the margins of the cartridge 16 or the well 14. The vacuum pump 30 is started and the control valve 40 is opened communicating the vacuum to the well 14 at the underside of the cartridge 16. Through the bores 44 in the template 42 the vacuum is communicated to the openings 24 in the cartridge 16. The surgeon or assistant locates a cultivated graft 18 closely above a selected opening 24 whereupon the vacuum draws the graft 18 into the opening 24. In that the opening 24 is sized to closely nest the graft 18, once the graft 18 is placed over an opening 24, the vacuum draws the graft down into the opening 24. The template 42 prevents the graft 18 from being drawn completely through the opening 24. In a similar manner, the remainder of the chosen openings 24 of the cartridge 16 are loaded with a graft 18.

To reduce the drawing of air past grafts 18 which have been loaded, the operator may selectively operate the valve 40 to simultaneously draw multiple grafts 18 into openings 24 or to only open the valve 40 for the period of time necessary to draw in a graft 18. Alternatively, the operator can use a transparent shield 46 which is positioned to cover loaded openings. Thus, as the operator loads openings 24 with grafts 18, the shield 46 is located over the openings 24 to protect the grafts 18 and prevent the needless drawing of air across the grafts 18 which may increase the risk of infection or effect the viability of the graft 18.

As a further embodiment, the vacuum pump 30 may communicate with a moveable manifold (not shown) which the user can position to only impose a vacuum at certain of said openings.

While I have shown and described certain embodiments of the present invention it is to be understood that it is subject to many modifications without departing from the spirit and scope of the appended claims.

I claim as follows:

1. A device for loading hair grafts in a cartridge of the type having a plurality of openings each adapted to retain a hair graft for subsequent transplantation comprising:

a fixture adapted to hold the cartridge;

means for imposing a pressure differential across the cartridge to urge grafts into said openings; and a blocking template attached to said fixture and including at least one bore located to registerwith said openings, said bore having a dimension to prevent a graft from being urged by the pressure differential from the cartridge openings.

2. The device of claim 1 further including means to control the imposition of the pressure differential between an on and an off condition.

3. The device of claim 1 wherein the pressure differential imposing means is a vacuum pump.

4. The device of claim 3 wherein the pressure differential imposing means comprises a manifold, said device further comprising means to index said manifold to terminate communication of said vacuum with openings loaded with grafts.

5. A method for loading hair grafts into a cartridge of the type having a plurality of openings each adapted to receive a graft, said method comprising:

imposing a pressure differential across cartridge openings;

positioning a graft to be urged by said differential into a selected opening; and capturing the positioned graft in the opening.

6. The method of claim 5 including imposing the pressure differential as a vacuum.

7. The method of claim 6 including capturing the graft by providing a blocking template at one side of the opening, said template having a bore to communicate the vacuum therethrough to the opening and block the drawing of the graft by the vacuum from the opening.

* * * * *